United States Patent [19]

Noeller

[11] Patent Number: 4,784,947
[45] Date of Patent: Nov. 15, 1988

[54] FLASH-PHOTOMETER FOR NEPHELOMETRIC DETERMINATIONS

[76] Inventor: Hans G. Noeller, 1942 Deerpark Dr., #92, Fullerton, Calif. 92631

[21] Appl. No.: 611,913

[22] Filed: May 18, 1984

Related U.S. Application Data

[63] Continuation of Ser. No. 281,220, Jul. 7, 1981, abandoned.

[30] Foreign Application Priority Data

Jul. 10, 1980 [DE] Fed. Rep. of Germany ....... 3026089

[51] Int. Cl.$^4$ .......................... C12Q 1/20; C12Q 1/06; C12M 1/34
[52] U.S. Cl. ...................................... 435/33; 435/39; 435/291; 435/808; 422/65; 422/73
[58] Field of Search ....................... 435/29, 31, 32, 33, 435/34, 39, 40, 291, 808, 809; 422/65, 73; 356/317, 318, 417, 337

[56] References Cited

U.S. PATENT DOCUMENTS

| | | | |
|---|---|---|---|
| 2,436,145 | 2/1948 | Johnson | 18/14 |
| 3,509,026 | 4/1970 | Sanders | 195/103.5 |
| 3,574,063 | 4/1971 | Bowman | 435/808 |
| 3,627,431 | 12/1971 | Komarniski | 356/246 |
| 3,666,631 | 5/1972 | Rich et al. | 435/808 |
| 3,832,532 | 8/1974 | Prazlin et al. | 435/32 |
| 3,928,140 | 12/1975 | Wyatt | 435/29 |
| 4,027,979 | 6/1977 | Komarniski | 356/180 |
| 4,133,873 | 1/1979 | Noller | 250/458.1 |

FOREIGN PATENT DOCUMENTS 3006028 8/1980 Fed. Rep. of Germany .
100085 5/1973 German Democratic Rep. .

OTHER PUBLICATIONS

Brunsting et al., The Review of Scientific Instruments, 43(10), 1514-1519 (1972).
Lunar, Anal. Biochem., 23:357-358 (1968).

*Primary Examiner*—Esther M. Kepplinger
*Attorney, Agent, or Firm*—Knobbe, Martens, Olson and Bear

[57] ABSTRACT

A method and apparatus for photographically recording and determining fluorometric and nephelometric analysis are described.

5 Claims, 1 Drawing Sheet

FLASH-PHOTOMETER FOR NEPHELOMETRIC DETERMINATIONS

This application is a continuation of application Ser. No. 281,220, filed 7/7/81 now abandoned.

TECHNICAL FIELD

This invention relates to chemical analytical instruments, generally, and more particularly to nephelometric and fluorometric devices.

BACKGROUND

In the last decade, a large number of very costly devices have been disclosed which are effective in turbimetric, nephelometric and fluorometric analysis and for the automatic transfer of data of these analysis values onto paper. Many of these devices fill the highly specialized tasks set for them in the field of research and in larger clinical facilities. However, a major portion of routine tasks in the field of medicine cannot be handled with these devices in an economical manner. For example, the small clinical laboratory or the physician's office laboratory cannot afford these extremely expensive automated analytical instruments. Thus, no fully satisfactory auxiliary device for determining antibiotic susceptibility has been available to the physician up to this point in time.

The availability of many different and new antibiotics and the necessity for determining the best suited antibiotic for combating a particular bacterial strain isolated from a patient have prompted the demand for a highly sensitive, simple and consequently inexpensive, yet extremely reliable antibiotic susceptibility determination method, which will furnish the results within a few hours after obtaining the sample for tests.

SUMMARY OF THE INVENTION

It is a principal feature of this invention to provide a simple, hence not a very involved method for determining nephelometric and fluorometric data. The method uses a pulse flash of light, from an electronic flash device, i.e. a strobe light as a light source. The method is extremely sensitive and is particularly suited for the quick determination of the susceptibility of germs to particular antibiotics, within a very short period of time and without significant effort or expense. Thus, the invention makes available the result of tests within a short time of obtaining the testing sample. Furthermore, the test result is in the form of a photographic document which can be visually or photometrically read, and can be stored for future reference. Typically, the photographic document is a picture on paper, i.e. a thin photographic film on a paper substrate, such as a Polaroid photographic print.

In one feature, the present invention comprises the method of recording nephelometric and fluorometric radiation from a plurality of samples in containers which are of substantially identical geometry. A plurality of these samples are arranged to receive substantially identical quantities and intensity of activating radiation in a first direction from a light source. A photosensitive film, which may be a self-supporting transparent film or a film of photosensitive material on a substrate, such as a self-developing photographic print, e.g. a Polaroid print, is arranged to receive light radiated from the samples in a second direction, the second direction being substantially perpendicular to the first direction in which the activating radiation strikes the sample. The light source is actuated to cause the strobe source to emit a pulse of short duration but high intensity light in the first direction into the samples. The film is exposed during the pulse to light radiated from all of the samples. The light produces different degrees of exposure in the photographic film, which, when the film is developed, results in differing optical densities. The optical density of the developed photosensitive film is proportional to the intensity of the light radiated by the respective samples. The radiated light results, of course, from the activating light. The radiated light may be of fluorometric radiation, in which the activating light photochemically activates a component of the sample, or it may be reflected light as in conventional nephelometric and turbimetric determination.

The method as described is particularly applicable to the screening of antibiotics to determine the efficacy of respective antibiotics against bacteria, in inhibiting the growth of bacteria in a medium. In this application, a series of samples, each innoculated with a sample of the bacteria and each containing a respective antibiotic, plus such additional control samples as may be desired, are prepared in containers of the same geometry. Typically, these containers could be vials of the same size and configuration. The samples are incubated for a predetermined period. All of the samples may be incubated for the same period of time, or different times may be used. The samples are then arranged in a predetermined relationship with each other and exposed to the activating radiation and the radiation is recorded on film as described above. By corresponding to the respective samples, the physician, or clinical laboratory technician can readily determine the relative inhibitive power of the respective antibiotic against the bacteria in question.

The present invention also contemplates a particular apparatus for accomplishing the methods referred to above. The apparatus comprises a sample holder which is constructed and disposed to hold a plurality of uniform geometry sample containers. The light source, which is characterized in that when actuated it emits a short duration, high intensity pulse of light, is constructed and arranged for directing a beam of pulsed-activating light from the source in a first direction into the samples. Directing means are provided which are so constructed and configured as to cause all of the samples to be exposed to substantially the same quantity and the same intensity of activating light when the source is pulsed. Photographic recording means, which includes some means for positioning a photographic film in a predetermined relationship with respect to the samples, such that when the apparatus is in use and the light source is pulsed, the pulsed activating light strikes all of the samples in the first direction, and all of the samples radiate light in a greater or lesser amount depending upon their composition, resulting from this activating light in a second direction to simultaneously expose the film to the light radiated by the respective samples in the respective sample containers, which are in the holder. The recording means is constructed and configured such that the second direction is substantially perpendicular to the first direction.

DESCRIPTION OF THE BEST MODE

Figure 1:
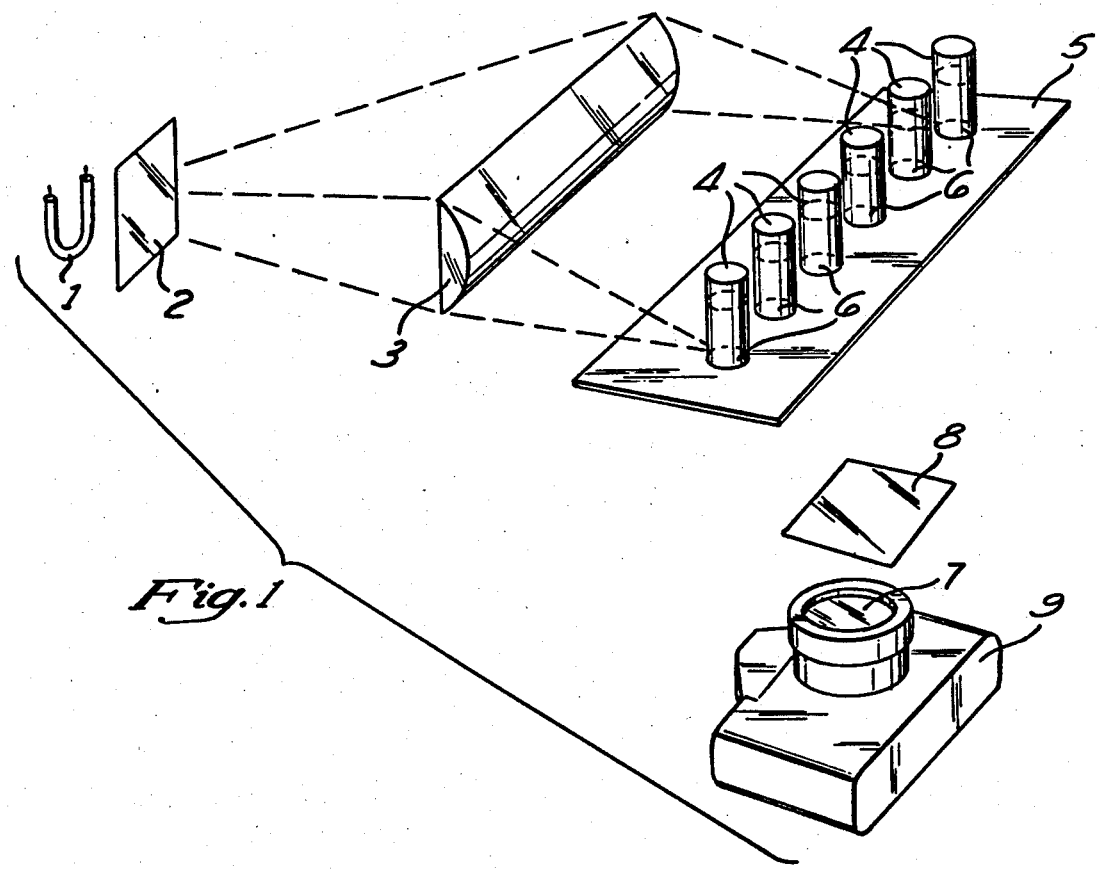
FIG. 1 is a schematic diagram of the apparatus of this invention.

A simple, tested and proven exemplified embodiment of the device, and of the method, for execution of tests in accordance with the present invention is described below, and the operation thereof will be discussed with reference to the drawings. This is an exemplary embodiment, however, it is not limiting.

A light source 1 such as a photo-flash or strobe light, e.g. a xenon photographic flash device, is arranged such that activating light is passed through a monochromatic filter 2. When the apparatus is used for fluorometric determinations, the transmission wave length of the filter, such as an interference filter, corresponds to the excitation wave length of the substance to be tested. The monochromatic activating lot is conducted through a cylindrical end of large surface area 3, which projects the monochromatic pulsed light beam onto a series of uniform geometry sample containers, e.g., flat-bottom glass test tubes 4, which are arranged with their longitudinal axis perpendicular to the first direction in which the activating light is incident thereon. This activating illumination which is incident on the sample containers and in the sample is focused, or collimated, approximately 10 mm above the bottom of the glass test tubes, perpendicular to the axis of the glass test tubes which are the sample containers.

The sample containers, the glass test tubes, stand on a transparent plate 5. The transparent plate 5 may be of glass or a transparent plastic. The plate is blackened with the exception of the surfaces 6 where the sample containers, the flat-bottom test tubes, are individually positioned. Thus, this plate functions simultaneously as the front face of a photographic recording means such as a Polariod camera 9. The camera lens 7 is located below the front face of the camera as is the camera shutter and a slide holder for a light filter 8. When the device is used for fluorometric determinations, an emission filter is placed into the slide holder. The emission filter corresponds to the emission wave length of the substance to be tested. The lens of the camera is mounted to the above-mentioned flat plate, so as to be focused about 10 mm above the bottom of the plate 5.

When used for fluorometric determinations, the required excitation and emission filters are introduced into the apparatus and the samples are placed in containers positioned adjacent to one another.

Simultaneously, with the one-time or multiple actuation of the light source, to get a one-time or multiple flash release, the shutter is opened. Light is radiated from each of the samples in a second direction, with is substantially perpendicular to the direction of the incident activating light and exposes the film simultaneously to the light radiated from all of the samples. Subsequently, the picture, which is obtained with conventional photographic techniques or with high speed picture developmenting techniques, such as the Polariod instant camera, can be removed. Density can be optimized through diaphragm adjustment.

On the photographic film, disc-shaped circular zones of variable density, or darkening, show up. The degree of optical density is directly dependent upon the concentration of the fluorescent substance in the sample. The optical density can be subjectively evaluated by simple visual observation, or can be ascertained more precisely with conventional optical density or reflected light measuring devices.

When the device is used for determination of nephelometric data, all that is required is the insertion of a single light filter for the purpose of monochromatization and consequently for the fullfillment of Beer's law.

Example

The following procedure has given good results in the determination of antibiotics susceptibility in a number of tests.

Sterilized, cylindrical flat-bottom glass test tubes with an inside diameter of slightly more than ¼ inch are filled with a nutrient solution, e.g. 1000 $\mu$l standard Trypticase or other standard nutrient solution. A $\mu$l sample of saturated pure or mixed liquid culture of bacteria-containing material obtained from the patient is introduced into the solution.

In this application, a different antibiotic is added to each of the tubes which are filled to a uniform level, except one tube which serves as the control. This is done very simply, for example, by adding an antibiotic disc, i.e. a small sheet of blotting paper with a diameter of about ¼ inch which has been treated with a standard quantity of antibiotic. A broad spectrum of different antibiotic sensitivity discs are presently available commercially for susceptibility determinations.

Because this method is extremely sensitive, discs with a very low content of effective ingredient are used. For example, discs charged with 0.5 mcg Tetracycline have been effective.

The tubes are incubated for a predetermined period of time e.g. 120 minutes or 90 minutes and a desired temperature, typically about 37° centigrade. The antibiotic discs are removed from each of the tubes and tubes are placed on the contact surfaces 6 of the plate 5 of the apparatus as previously described. Using a Polariod camera 9, as the photographic recording means, after actuation of the light source to produce a flash and appropriate illumination of the photographic film, e.g. the instant print or other picture is developed. Almost instant results are available using the self-developing photographic print technique, e.g. a Polariod camera.

Figure 2:
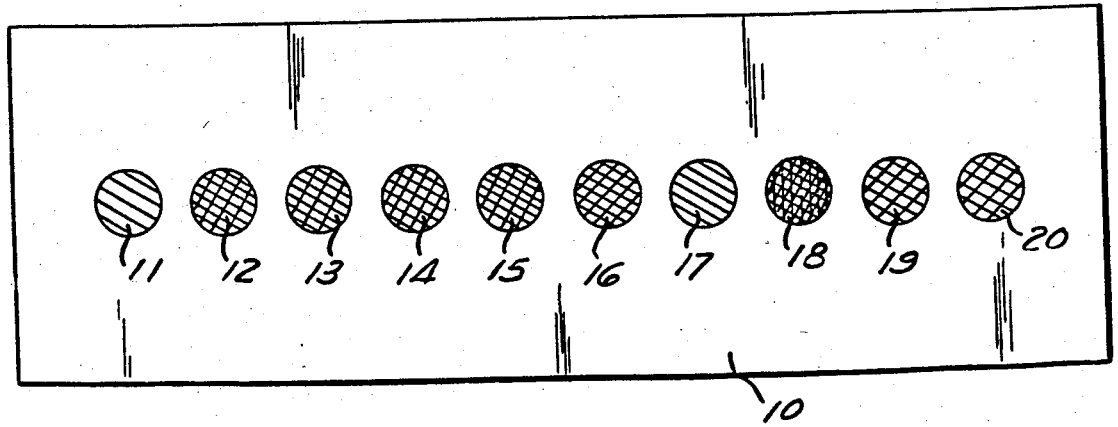
FIG. 2 is a schematic representation of a photo sensitive film, such as a photographic print in which the film is carried on a flat substrate, e.g. Polaroid print, showing the print optical density of the respective samples by means of fewer or greater lines in different configurations to give the indication of greater or lesser optical density.

A series of blackened discs, i.e. a series of discs with different optical densities, is obtained using the different antibiotics. The antibiotic which produces the highest degree of optical density in the positive image is the optimum suited antibiotic. The lowest degree of optical density is assigned to the control tube. Here the bacterial growth has remained uninfluenced, unrestricted, during the incubation period and the bacteria multiplied to a very high degree, as determined by the increased diffusion of light, and have furnished the highest reproduceable nephelometric effect. This can be determined by subjective visual examination, or the optical density of the various individual zone can be objectively ascertained by conventional photometric devices. These differences in optical density are schematically depicted in FIG. 2. FIG. 2 shows a photographic film, e.g. a Polariod print in which the film is on a paper substrate, and depicts ten disc-shaped fields of differentiatable optical densities or darkening. Nine of these, i.e. 12 through 20 have been brought about by testing samples containing different antibiotics. Zone 11, the disc-shaped zone with the least optical density, or darkening, is the control sample. The highest degree of optical density is in field 18, which corresponds to the sample containing Tetracycline. Among the samples which have been charged with comparable doses of antibiotics, the Tetracycline has brought about the greatest effect. It will be apparent from the foregoing discussion and the description of the process and apparatus of this invention that the present method of nephelometric and fluorometric determinations, using a flash tube as the light source, provides an extremely high degree of brightness and sensitivity and makes it possible to obtain a very high sensitivity when the device is used for fluorometric determinations as well as for nephelometric determinations, in spite of the fact that the apparatus and the auxiliary testing devices are relatively inexpensive. Another advantage of the method is that it furnishes objective documents in the form of photographs which can be subjectively evaluated in a simple and effortless manner, or which can be objectively evaluated at any time without any difficulty using optical density photometric means.

Since the method is based upon the extremely high intensity of the light pulse, the method designed according to this invention is eminently suitable for the determination of the susceptibility of bacteria with respect to various antibiotics and consequently is eminently suited for the selection of the most suitable antibiotic for a given patient to combat a specific bacterial strain or bacterial infection. The invention is not limited to this particular application, however.

The nephelometric determination of even minimal bacteria growth using the method described here allows one to select the most suitable antibiotic at a much earlier time than has been possible using the presently available methods.

With these advantages in mind, it will be understood that this present invention is not limited to the specific technique, process, or structures described above, which are exemplary, but only by the scope of the claims as appended hereto.

Industrial Application

This invention finds industrial application in clinical medicine.

What is claimed is:

1. A method of screening antibiotics to determine their efficacy against bacteria by testing respective antibiotics for growth inhibiting effect against said bacteria, said method comprising the steps of:
   preparing a series of samples in container of the same geometry, including the bacteria in question and, in the respective samples, different antibiotics;
   permitting said samples to incubate for predetermined periods before exposure to a high intensity light source;
   arranging said sample containers in a fixed predetermined relationship to each other and to said light source to permit all of said samples to receive substantially identical intensity of activating radiation in a first direction from said light source;
   arranging a photographic film to receive light radiated from all of said samples in a second direction substantially perpendicular to said first direction;
   actuating the light source to emit a short duration pulse of activating radiation in said first direction simultaneously into each of said samples;
   exposing said film simultaneously to light radiated in said second direction from said samples so as to provide on the film, when developed, a series of zones corresponding to the respective samples and of various degrees of exposure;
   comparing the optical density of said zones as an indication of the inhibition of said bacteria by the respective antibiotics; and
   selecting as the most appropriate antibiotic for combatting said bacteria the antibiotic in the sample which produces the highest degree of optical density in the positive image of the film, or conversely, the lowest degree of optical density in the negative image of the film.

2. A method for determining the susceptibility of bacteria to antibiotics which comprises:
   arranging a plurality of samples of liquid solutions comprising said bacteria and various antibiotic compositions in containers having substantially the same geometry;
   simultaneously exposing each of said samples to a high intensity pulse of light in a first direction to cause light to radiate from said samples in a second direction;
   exposing a photosensitive film to said radiated light to produce a plurality of zones of various degrees of exposure on said film corresponding to said samples;
   comparing the optical density of said zones on the developed film as an indication of the susceptibility of said bacteria to said antibiotic compositions; and
   assessing the most appropriate antibiotic and selecting it for use.

3. A method as claimed in claim 2, wherein said second direction is substantially perpendicular to said first direction.

4. A method as claimed in claim 2, further comprising;
   including a control sample in a container having the same geometry as said containers;
   exposing said control sample with said other samples to said pulse of light to cause light to radiate from said control sample in said second direction;
   exposing said film to said light radiated from said control sample and said other samples; and
   comparing the optical density of said zones and a zone corresponding to said control sample as said indication of the susceptibility of said bacteria to said antibiotic compositions.

5. A method as claimed in claim 4, further comprising:
   incubating said sample before exposure to said light to allow the bacteria in said control sample to multiply to a very high degree.

* * * * *